United States Patent [19]

Chang

[11] Patent Number: 4,680,098

[45] Date of Patent: Jul. 14, 1987

[54] AQUEOUS RECOVERY OF COBALT OR COBALT AND MANGANESE FROM SOLUTION ALSO CONTAINING OXYGENATED AROMATIC COMPOUNDS

[75] Inventor: Yuehsiung Chang, Naperville, Ill.

[73] Assignee: Amoco Corporation, Chicago, Ill.

[21] Appl. No.: 850,534

[22] Filed: Apr. 11, 1986

Related U.S. Application Data

[63] Continuation-in-part of Ser. No. 712,975, Mar. 18, 1985.

[51] Int. Cl.$^4$ ............................................ B01D 13/02
[52] U.S. Cl. .............................. 204/182.4; 204/151; 204/301
[58] Field of Search ................... 204/182.4, 151, 301; 210/748

[56] References Cited

U.S. PATENT DOCUMENTS 4,311,521  1/1982  Harper et al. ................... 75/101 BE

FOREIGN PATENT DOCUMENTS 0012158  2/1978  Japan ................................ 204/182.4

Primary Examiner—John F. Niebling
Assistant Examiner—Terryence Chapman
Attorney, Agent, or Firm—Frederick S. Jerome; William H. Magidson; Ralph C. Medhurst

[57] ABSTRACT

Cobalt and manganese oxidation catalyst metals are recovered from trimellitic anhydride process residue by extracting the residue with water and using the extract solution as a diluting solution in an electrodialyzer the separation stack of which comprises an anode channel and at least one three channel repeating unit wherein each repeating unit having in sequence channels A, B, and C. In this separation stack the anode channel is formed by an anode and a cation permeation membrane, Channel A is formed by two cation permeation membranes, Channel B is formed by a cation permeation membrane and an anion permeation membrane, and Channel C is formed by an anion permeation membrane and either a cation permeation membrane or a cathode. A suitable anolyte flows through the anode channel. The diluting solution is fed to the A channels. An electrolyte is fed to the B channels. A suitable catholyte is fed to the C channels. Concentrating solution of cobalt and manganese substantially free of metal and organic contaminants is effluent from the B channels.

The metals cobalt or cobalt and manganese can be recovered as an aqueous solution of acetate salts from an aqueous solution containing aromatic compounds including benzoic acid and one or more of the toluic acid, phthalic acid, and carboxybenzaldehyde isomers by electrodialysis using acetic acid and the catholyte, water as the metal acetate solvent, and the aqueous solution acid oxygen-containing aromatic compounds, and the metal ions as a more efficient than precipitating the metals from such solution as their carbonates and dissolving the carbonate precipitate in acetic acid.

22 Claims, No Drawings

AQUEOUS RECOVERY OF COBALT OR COBALT AND MANGANESE FROM SOLUTION ALSO CONTAINING OXYGENATED AROMATIC COMPOUNDS

RELATED APPLICATIONS

This is a continuation-in-part of Ser. No. 712,975 filed Mar. 18, 1985.

FIELD OF THE INVENTION

This invention relates to an electrically driven process for recovery of cobalt or cobalt and manganese in the acetate form thereof from an aqueous solution containing ions of such metal or metals and dissolved benzoic acid and one of the isomers of toluic acid, phthalic acid and carboxybenzaldehyde.

BACKGROUND OF THE INVENTION

Electrodialysis is a generally known electromembrane process for transport of ions through membranes as a result of an electrical driving force. In an electrodialytic process using nonselective membranes that are permeable to ions, electrolytes can be separated from nonelectrolytes. If the membranes are more permeable to anions than to cations or vice versa, e.g., ion-exchange membranes, the concentrations of ionic species in solution can be decreased or increased by electrodialysis. Thus practical depletion or concentration of electrolyte solutions is achieved.

In an electrodialyzer a number of cation-selective and anion-selective membranes are arranged between a pair of electrodes so that the electrodes and one or more membranes form a multiplicity of parallel solution channels. With multichannel electrodialysis, irreversibilities represented by decomposition potentials at the electrodes can be distributed over many channels and thus minimized. Problems of handling products formed at the electrodes can be minimized as well.

An electrodialysis stack in an electrodialyzer comprises an alternating array of cation and/or anion permeation membranes which together with end caps and seal supports limit compartments or channels. End caps and seal supports are non-conductive and liquid impermeable and are joined to form an outer boundary of a stack. End compartments or channels are defined by an end cap and a membrane. Disposed within one end channel is a suitable anode and disposed within the opposite end channel is a suitable cathode. Anode and cathode are connected to positive and negative terminals of a suitable electrical power source respectively for a required supply of direct current. The anode-containing channel has flowing therein an anolyte and the cathode-containing channel is for the flow of a catholyte.

An industrial electrodialysis stack can be of any well known type of membrane assembly such as a plate and frame type assembly containing a plurality of planar membranes in parallel spaced relations with about one millimeter space between each membrane. The electrodialysis stack can have a number of repeating separation units which typically vary in configuration from two to five channels per separation unit depending upon the character and nature of the ions being transported for separation, the transporting solvents and electrolytes. The order of cation permeation and anion permeation membranes in each repeating unit will vary with the separation or separations to be effected.

After the recovery of cobalt or cobalt and manganese starting by water extraction of a residue of the process for manufacture of isophthalic acid or for example, from U.S. Pat. No. 2,964,599 or British Patent Specification No. 1,413,829, terephthalic acid is known, while some manufacturers of said phthalic acids use the aqueous extract solution as a source of the cobalt or cobalt and manganese metal oxidation catalyst even though such solution contains small amounts of the oxygenated aromatic compounds and even smaller amounts of compounds having an adverse affect on the quality, especially color, of the phthalic acid product. Other manufacturers of such phthalic acids elect to precipitate metal catalyst carbonate from solution and dissolve the metal carbonate in acetic acid as a means for eliminating the return of oxygenated aromatic Co and by-products to oxidation.

Isophthalic acid or terephthalic acid are manufactured by the air oxidation at a temperature above 150° C. of liquid m-xylene or p-xylene in the presence of an acetic acid solution containing ions of cobalt or cobalt and manganese as oxidation metal catalysts together with a promoter therefor which can be either bromide ions, or acetaldehyde or methyl ethyl ketone. The fluid oxidation effluent, which is a suspension of isophthalic acid (IPA) or terephthalic acid (TPA) as crystalline product in an acetic acid solution containing in addition to catalyst metals inter+ alia+ dissolved IPA or TPA and, oxygen-containing aromatic compounds including benzoic acid one or more of the isomers of toluic acid and carboxybenzaldehyde. The fluid effluent is cooled to a commercially feasible temperature of from 100° C. down to about 50° C. to precipitate additional IPA or TPA and then subjected to solid-liquid separation means to recover a crystalline IPA or TPA product, and acetic acid mother liquor still containing catalyst metal ions, some IPA or TPA and the other oxygen containing aromatic compounds. The acetic acid mother liquor is distilled to remove its water (by-product of the oxidation) and most of the acetic acid as a mixture as feed for fractionation to recover acetic acid of 3 to 5 weight percent water and reject the by-product water. The distillation bottoms product contains about 30% to 40% solids which comprise the catalyst metals, IPA or TPA and the other oxygen-containing aromatic compounds and 60% to 70% by weight solvent which is 90% acetic acid and 10% water. The distillation bottoms is one residue which can be treated according to the process of this invention. But such distillation bottoms can be further heated to evaporate substantially the 70% solvent to a liquid residue fluid at a temperature of 115° to 125° C. Such 115° C. to 120° C. fluid residue can also be treated according to the process of this invention.

The present invention replaces said carbonate precipitation and acetic acid redissolving by electrodialysis and substitutes the consumption of a small amount of electrical energy for the rather large cost of the precipitating sodium carbonates and redissolving acetic acid.

We are not aware of any prior publication which discloses the electrodialysis separation of catalyst metals from the oxygen-containing aromatic compounds or publications from which one skilled in the art of separating such metals from solution also containing the oxygen-containing aromatic compounds could perceive the electrodialysis separation comprising the main feature of the present invention.

Trimellitic anhydride (TMA) is produced from pseudocumene (1,2,4-trimethylbenzene) by its oxidation with molecular oxygen to trimellitic acid (TMLA) in an acetic acid solution containing as components of catalyst the following: ions of bromine in combination with either ions of cobalt, manganese and zirconium, or with ions of cobalt, manganese and cerium, or with ions of cobalt, manganese, cerium and zirconium. Such oxidation processes are described in U.S. Pat. Nos. 3,491,144, 3,532,746 and 3,683,016 all of which are incorporated by reference.

Impure TMLA is recovered from the oxidation effluent, which is typically an acetic acid solution comprising components catalyst, TMLA, mono- and dimethyl benzoic acid, unsubstituted benzoic acid, ortho-, iso- and terephthalic acids, methylphthalic acids, and carboxybenzaldehydes, by crystallization from such solution followed by solid-liquid separation. Impure crystalline TMLA is washed with acetic acid and melted to form impure TMA which is distilled to a high purity product. The acetic acid mother liquor is distilled to remove acetic acid and water as a distillate which is then fractionated to obtain an acetic acid product containing 3 to 5 weight percent water. Residues from distillation of impure TMA and residues from distillation of acetic acid mother liquor contain catalyst components and a substantial amount of TMA as well as materials boiling lower and higher than TMA.

Another technique for recovery of TMA is distillation to remove water and acetic acid from acetic acid solution effluent from the oxidation of pseudocumene. Such distillation also converts TMLA to TMA by dehydration. Thereafter, the resulting mixture, which is impure TMA, is distilled to remove TMA. A modification of the foregoing recovery technique involves adding the acetic acid solution oxidation effluent to liquid impure TMA which is maintained just above its melting point temperature. The acetic acid and water in this case are flashed off as a vapor product which can be used as feed to the fractional distillation recovery of acetic acid from water. Impure TMA liquid is drawn off and distilled to recover high purity TMA.

Both of the foregoing final distillations of impure TMA leave a catalyst metal-containing residue having also oxygenated aromatic compounds boiling higher than the boiling point of TMA. Such a mixture of metal-organics and higher boiling oxygenated compounds must contain a substantial amount of TMA to have the residue liquid at reasonable temperatures, such as 180° C. to 235° C.

Such TMA process residues contain various components of which some are water-soluble and others are water insoluble in from 0.25 up to 6 weight parts, usually 0.6 up to 3.0 weight parts, of water per 1.0 weight part of residue at temperatures of from 25° C. up to 100° C. Extraction of TMA process residues with such amounts of water at said temperatures will dissolve: more than 90 percent of the catalyst metals which are present as organo-salts, substantially all of the inorganic and organic bromides, substantially all of the TMA as its hydrated TMLA triacid analog, and some of the acidic oxygen-containing co-products, e.g., benzoic acid and ortho-toluic acid. The insoluble oxygen containing co-products include iso- and terephthalic acids, toluic acids aldelhydo-benzoic and phthalic acids and carboxy- and aldelhyo-esters which are also oxygen-containing derivatives of pseudocumene.

Many techniques have been proposed for the recovery of catalyst metals from such aqueous extract solutions. For example, sodium carbonate per se or the mixture thereof with sodium bi-carbonate are added to the solution to precipitate at pH of 7 to 8 the carbonates of at least cobalt and manganese. The precipitate is recovered and dissolved in acetic acid to regain those catalyst metals as their acetates for reuse in the oxidation of pseudocumene. This recovers the catalyst metals but not the dissolved TMLA. British Patent Specification No. 1,413,829 describes such a catalyst recovery.

U.S. Pat. No. 4,284,523 which is incorporated by reference, describes a method of treating the TMA process residue with water. The residue is extracted with from 0.35 up to 1.5 weight parts of water per weight part of residue at a temperature of from 70° C. up to 100° C. Then, with or without first separating water-in-solubles, the mixture or first solution is either diluted with additional water without change of the 70° C. to 100° C. temperature and the diluted mixture is cooled to a temperature of 20° C. to 35° C. or the first solution is cooled to a temperature of 20° C. to 35° C. and diluted with additional water without change of that 20° to 35° C. temperature. Such dilutions precipitate dissolved solids. Finally, either of the 20° C. to 35° C. mixtures is subjected to solid-liquid separation techniques to recover some aqueous solution of catalyst metals separate from insolubles and precipitates. In either of said dilutions, the amount of water used is the amount required to percipitate 15 percent to 20 percent of the dissolved high boiling oxygen-containing aromatic compounds. Said technique has for its purpose the limiting of high boiling oxygen-containing aromatic compound contamination of reusable catalyst metals.

The final 20° C. to 35° C. aqueous solution filtrate can be treated with carbonates to first selectively precipitate iron, if present as a contaminating corrosion metal, and then at higher pH precipitate cobalt annd manganese. The 20° C. to 35° C. separated aqueous solution can alternatively be treated with a cation exchanger followed by elution of the exchanger with a strong inorganic acid to remove catalyst metals from the cation exchanger and regenerated as disclosed by U.S. Pat. No. 4,298,759. Also the separated 20° to 35° C. temperature aqueous solution can be contacted with one side of a cation permeable membrane the other side of which is contacted with a hydrohalidic acid whereby the catalyst metal ions migrate through the membrane into said acid which carries the metals as halide salts as disclosed in U.S. Pat. No. 4,311,521.

The foregoing catalyst metal reclaiming process of U.S. Pat. No. 4,311,521 uses the cation permeable membrane in a dialysis separation step, but is not effective with acids other than hydrohalidic acids. The separation process of U.S. Pat. No. 4,311,521 functions on the basis of a transfer of metal cations through the membrane from an aqueous feed solution to the hydrohalidic solution and the transfers therefrom of hydrogen cations through the membrane to the aqueous solution. Such transfers are apparently not dependent on the use of a conductive solution and are not effective when acetic acid is substituted for the hydrohalidic acid solution.

In the manufacture of trimellitic anhydride, the intra-molecular anhydride of trimellitic acid or 4-carboxyphthalic anhydride, by the procedure before described, the residue product can contain from 50 to 80 weight percent trimellitic anhydride and can amount to from 16% to 26% of the anhydride product recovered. Such residues can also contain from 0.3 up to 2.5 weight percent cobalt (calculated as the metal) and manganese in an amount of from 0.24 to 0.6 times the cobalt. The cerium, when present, will be about equal to manganese. The zirconium, when present, will be 0.01 to 0.1 times the cobalt content. It is important to recover cobalt from the residue because the cobalt metal has had a market value of forty dollars per pound within the last ten years. Environmental and economic considerations require recovery of catalyst metals.

Trimetallic anhydride process residues suitable for treatment by th method of the present invention typically contain from 50 up to 85, preferably 65 to 85, weight percent trimellitic acid and intramolecular anhydride as flux for materials boiling higher than the trimellitic anhydrides including the organo-metal compounds containing the extractable catalyst metals. The process is useful for compositions shown in Table I (below):

TABLE I
TRIMELLITIC ANHYDRIDE PROCESS RESIDUE

| Component | Concentration, wt. % |
| --- | --- |
| Acetic Acid | 0 to 5.0 |
| Benzoic Acid | 0 to 5.0 |
| Toluic Acids | 0 to 5.0 |
| Phthalic Acids | 0.25 to 15. |
| Other Lower Boiling Compounds[1] | 0.5 to 5. |
| Trimellitic Acid and Anhydride | 50 to 85 |
| Other Higher Boiling Compounds[2] | 0.25 to 5 |
| Cobalt[3] | 0.3 to 2.5 |
| Manganese[3] | 0.07 to 1.5 |
| Cerium[3] | 0 to 1.5 |
| Iron[3] | 0.01 to 0.06 |
| Zirconium[3] | 0.01 to 0.25 |
| Sodium[3] | 0 to 1.2 |
| Bromine[3] | 0.2 to 2.5 |

[1]"Other Lower Boiling Compounds" are those unnamed boiling lower than trimellitic anhydride.
[2]"Other Higher Boiling Compounds" are those unnamed boiling higher than trimellitic anhydride.
[3]Analysis for sodium by atomic absorption, all of the other elements by x-ray diffraction.

SUMMARY OF THE INVENTION

Cobalt or cobalt and manganese oxidation catalyst metals are recovered from an aqueous solution containing dissolved oxidation metals catalyst from dissolved oxygen-containing aromatic compounds including, inter alia, benzoic acid, and one or more of the isomers of toluic acid, phthalic acid and carboxybenzaldehyde by using the aqueous solution as a diluting solution in an electrodialyzer the separation stack of which comprises an anode channel and at least one three channel repeating unit wherein each repeating unit having in sequence channels A, B, and C. In this separation stack the anode channel is formed by an anode and a cation permeation membrane, each Channel A is formed by two cation permeation membranes, each Channel B is formed by a cation permeation membrane and an anion permeation membrane, and each Channel C is formed by an anion permeation membrane and either a cation permeation membrane or a cathode. A suitable anolyte flows through the anode channel. The diluting solution is fed to the A channels. An electrolyte is fed to the B channels. A suitable catholyte is fed to the C channels. Concentrating solution of cobalt and manganese substantially free of metal and organic contaminants is effluent from the B channels.

BRIEF DESCRIPTION OF THE INVENTION

This invention is an electromembrane process for separation of catalyst metal components free of contaminant metal components and/or organic compounds from a residue produced during manufacture of an aromatic acid by a catalytic air oxidation of a suitable alkyl aromatic feed. More particularly, this invention is an electrodialysis process for recovery of cobalt and manganese ions from a diluting solution comprising said ions and contaminants, which comprises feeding said solution to an electrodialyzer separation stack which comprises an anode channel formed by an anode and a cation permeation membrane, and at least one, three-channel repeating unit wherein each repeating unit having in sequence channels A, B, and C wherein this repeating unit comprises a Channel A formed by two cation permeation membranes, a Channel B formed by a cation permeation membrane and an anion permeation membrane, and a Channel C formed by an anion permeation membrane and either a cation permeation membrane or a cathode passing an anolyte comprising an aqueous solution of an acid through the anode channel, feeding diluting solution through the A channels, feeding an electrolyte through the B channels, feeding a suitable catholyte through the C channels and removing a concentrate comprising a solution of cobalt and manganese substantially free of contaminants as an effluent from the B channels.

In a preferred method of operation, wherein cobalt and manganese are separated from contaminants comprising organic acids such as trimellitic acid, acetic acid, etc., hydrogen ions released from the anolyte are transported across the first cation permeation membrane into a diluting solution channel, and those not needed therein are in turn transported with the released metal ions across a second cation permeation membrane into a concentrating solution channel. Carboxylate ions, for example, acetate ions, in and released in the catholyte are transported across the anion permeation membrane into a concentrating solution channel and combine with the catalyst metals there in solution. Catalyst metals leave the stack as their carboxylate salts in the concentrating aqueous solution. A first cation permeation membrane between anode and diluting solution channels is necessary to prevent potential foaming of the feed extract solution by gases such as dioxygen ($O_2$) evolved at the anode. This first cation permeation membrane also provides protection of an anion permeation membrane in the adjacent repeating unit from fouling by aromatic anions in the feed extract solution.

Electrodialyzers useful in this invention consist of (i) a basic separation stack of narrow compartments or channels filled with electrolyte solutions whose concentration and/or composition is altered as a result of electromigration through membranes in contact with these solutions, and (ii) a suitable electrical power supply of a direct current potential for passing direct current through the whole stack. Typically a direct current potential of about 400 volts is useful in electrodialysis and readily available from commercial power supplies.

Terminal channels of a separation stack are bounded by electrodes. When electric current passes through the stack, cations tend to migrate toward the cathode and anions tend to migrate toward the anode. However, cations are blocked from further transfer through a stack by an anion permeation membrane, and anions are blocked similarly from further transfer by a cation permeation membrane. Thus ion-depleted and ion-enriched solutions can be withdrawn from specified channels. Any of several mechanically sturdy, highly conductive cation and anion permeation membranes now available commercially may be used in this invention, including Nafion 425 (DuPont), CMV & AMV (Asahi), MC 3470 and MA 3475 (Ionac.), preferably Nafion 425, MC 3470 and MA 3475.

In the present electromembrane process using a double exchange electrodialysis, it is preferred to separate an aqueous extract solution containing TMLA and catalyst compounds, among other water-soluble compounds from water-insoluble co-products before proceeding to the electrodialysis.

Preferably the TMA process residue, such as shown in Table I above, containing the oxidation catalyst and contaminant metals is prepared for use in this invention by extraction with water at temperatures in the range of about 25° C. to about 100° C. using about 0.25 to about 6 weight parts of water per 1.0 weight part residue, typically about 0.5 to about 6.0, preferably at least 1.0 weight parts of water per 1.0 weight part residue. If desired, the aqueous extract solution containing cobalt and manganese ions, contaminant metal ions such as iron, copper and/or nickel, and water-soluble organic oxidation products such as TMA, can be subjected to solid-liquid sepration techniques to recover an aqueous solution suitably free from insolubles and precipitates to be fed to a separation stack of the electrodialyzer. A complex forming compound (CFC) is preferably added to the aqueous extracting solution an amount sufficient to prevent substantial transport of iron, copper and nickel with cobalt and manganese ions into the concentrating solution. CFCs useful in this invention must have CFC-metal equilibrium constants for iron, copper and nickel which are higher than the equilibrium constant for CFC-cobalt and CFC-manganese. Particularly useful in the present invention as a CFC are compounds such as ethylene diaminetetra-acetic acid, ammonia diacetic acid, and ammonia triacetic acid. Ethylene diaminetetra-acetic acid (EDTA) is a preferred CFC.

Generally an anolyte useful in this invention comprises a dilute aqueous solution of an acid such as nitric, sulfuric, sulfurous, phosphoric, acetic, carbonic, and boric acid, preferably at a concentration of at least 0.01N. Preferred anolytes include sulfuric acid at a concentration in the range of about 0.01N to about 1N and acetic acid at about 4 percent to about 20 percent.

Electrolyte useful as a concentrating sweep solution fed to channels defined by a second cation permeation membrane and an anion permeation membrane, is a dilute aqueous solution of an acid such as hydroiodic, hydrobromic, hydrochloric, nitric, sulfuric, sulfurous, phosphoric, hydrofluoric, acetic, carbonic, hydrocyanic and boric acids preferably at a concentration of at least 0.01N. Preferred acids useful as a concentrating sweep solution in this invention are hydrobromic acid, at a concentration in the range of about 1N to about 0.01N and acetic acid at about 4 percent to about 20 percent.

Typically a catholyte useful in this invention comprises a dilute aqueous solution of an organic aliphatic acid having 1 to 20 carbon atoms such as formic acid acetic acid, For this invention a preferable catholyte is an aqueous solution of acetic acid having from about 4 percent to about 20 percent by weight acetic acetate.

According to this invention a process temperature of the electrodialyzer in a range of about 20° C. to about 100° C. may be used. Typically temperature separation stack operating temperature is in a range of about 25° C. to about 90° C. A preferred process temperature range of the electrodialyzer separation stack is about 45° C. to about 75° C.

In a preferred embodiment of this invention the concentrating solution of metal acetates in dilute acetic acid leaving the separation stack is suitably used per se to provide oxidation metal catalyst for the air oxidation of methyl-substituted benzenes, for example, toluene and the xylenes, in the liquid phase by the process of U.S. Pat. No. 2,833,816 which is incorporated by reference or such aqueous acetic acid solution of metal acetates is advantageously treated to separately recover cobalt by conventional means. For example by adjustment of the pH to about 4 to 5 which precipitates a basic iron acetate. Then the iron-free solution is contacted with one side of a cation permeation membrane, such as a fluoropolymer cation permeation membrane, the other side of which is in contact with hydrobromic acid. Addition of metallic manganese to the resulting solution of cobalt and manganese bromides in hydrobromic acid and adjustment of pH to about 6 precipitates cobalt metal for its separate recovery and ultimate reuse. Such a process is disclosed and suggested by U.S. Pat. No. 4,311,521.

The metal-free diluting extract solution leaving the separation stack can be concentrated, for example, by evaporation of about 50 percent to about 70 percent of the water, and the resulting concentrate cooled to 4° to 5° C. to precipitate a TMLA product which, preferably after acetic acid extraction to dissolve a further purified TMLA, can be added to the TMA process for additional TMA recovery.

Suitably, the trimellitic anhydride process residue is extracted with from about 0.5 to about 6, preferably at least 2.0 weight parts of water per 1.0 weight part of residue. Residue as produced is liquid at a temperature of from 230° C. to 235° C., and when mixed in the weight ratio of water to residue of about 1.0, about 20% of the residue remains undissolved at room temperature of 20° C. to 25° C. At weight ratio of water to residue of about 1.5 all the residue is and remains dissolved at 20° to 25° C. temperature but the resulting solution is quite viscous. To maintain a high concentration of dissolved catalyst metals and good processability it is preferred to use a weight ratio of water to residue of from 2 to 5.

An electrodialysis separation stack is operated with a direct current electric power source connected to the anode and cathode to impose a voltage which can be from 15 to 30 volts in a channel stack when the channels are 25 millimeters wide to from 2.5 to 4 volts when the channels are about 10 millimeters wide. Such voltages can provide a current density of from 20 to 25 milliamperes per square centimeter of membrane area. Such current densities are suitable for the separation process of this invention.

A four channel separation stack having three separation membranes in the sequence of (i) a first cation permeation membrane, (ii) a second cation permeation membrane and (iii) anion permeation membrane is the simplest form of electrodialysis stack useful in this invention. In this simple electrodialyzer the separation stack comprises an anode channel and only one, three-channel repeating unit having in sequence channels A, B, and C. In this separation stack the anode channel is formed by an anode and a cation permeation membrane, the Channel A is formed by two cation permeation membranes, the Channel B is formed by a cation permeation membrane and an anion permeation membrane, and the Channel C is formed by an anion permeation membrane and a cathode. Such a sequence of permeation membranes can be repeated to from a separation stack having one hundred or more channels. Industrial units can comprise any suitable number of these separation units.

According to a preferred embodiment of this invention, an anolyte consisting of a dilute aqueous solution, of about 4 percent to about 20 percent of acetic acid is fed to the anode channel. The aqueous extract solution or catalyst metal content portion of such solution is fed to each of the diluting channels. A dilute electrolyte of at least about 0.1N HBr is fed to each of the concentrating channels. A catholyte consisting of an aqueous solution of acetic acid at about 4 percent to about 20 percent is fed to the cathode channel.

In another specific embodiment the electrodialysis feed solution is obtained by water extraction of a residue from isophthalic acid or terephthalic acid manufacture with from 1 up to 6 weight parts of water per weight parts of residue. Since such residue can be, as before disclosed, at a temperature of above 100° C. up to a temperature of 115° C. to 125° C. which is well above the boiling point temperature of water and contact of such hot residue with water evaporates it, it is preferred to use sufficient water to contact the hot residue so that the final extract solution contains a weight ratio of water to residue of from 1:1 to 6:1. The extracting can be at a temperature of 15° C. up to 35° C. After contact between the hot residue and the extracting water, the resulting mixture of solution and insolubles is cooled to a temperature of from 25° C. to 50° C. The cooled mixture is subjected to means for solid-liquid separation, i.e., by filtration, settling, decantation, centrifugation, and the like. The following three examples of cooling and separation temperatures with their percent solids recovered and percent IPA product recovered are presented as a guide for design of these operation steps.

The following illustrative examples comprise the best mode of operating the present invention contemplated at the time of filing the present patent application.

EXAMPLE 1

A four channel stack described above is used in a batch recirculating mode. Cation permeation membranes are made of a polytetrafluoroethylene modified with sulfonic acid groups bonded to carbon atoms of the polymer chain, in this example Nafion 425 membrane a product of DuPont. The anion permeation membrane is an aminic sulfate modified polymer, in this example MA 3475 membrane a product of Ionac Chemical, Sybron Corporation. Total effective area of the three membranes is 46 square centimeters. Channel widths are 25 millimeters. Direct voltage imposed on the stack is 25 volts DC which provides a current density of 18 milliamperes per square centimeter ($mA/cm^2$).

An aqueous extract solution is prepared by solubilizing molten trimellitic anhydride process residue in water at a temperature of 40° C. in a weight ratio of water to residue of 2:1. All of the residue dissolves. The solution is cooled to the temperature of 25° C. Such solution at 25° C. does not yield precipitated water-insolubles upon weeks of standing.

Solutions used to circulate through anode, feed, product, and cathode channels are, respectively, 1000 ml of 5 weight percent sulfuric acid ($H_2SO_4$) content, 500 ml of trimellitic residue extract solution, 500 ml of 1 weight percent HBr solution, and 1000 ml of aqueous 20 weight percent acetic acid.

Results of this catalyst metal recovery are shown in TABLE II to follow.

TABLE II

| CATALYST METALS REMAINING IN EXTRACT SOLUTION AGAINST OPERATING TIME | | | | |
|---|---|---|---|---|
| | Cobalt | | Manganese | |
| Time hours | Concentration ppm | Current Efficiency, % | Concentration ppm | Current Efficiency, % |
| 0 | 1750 | — | 620 | — |
| 4 | 920 | 9.4 | 300 | 3.6 |
| 10 | 297 | 6.6 | 93 | 2.6 |
| 23 | 34 | 3.4 | <12 | 1.3 |

Catalyst ions only account for a fraction of the current passed through the cell. The remainder of the current is primarily carried by hydrogen atoms from the dissociation of TMLA and from water splitting at the anode. These hydrogen atoms eventually are transported to the concentrating solution of catalyst metals where the hydrogen atoms combine with acetate ions as acetic acid.

In this example, recoveries of cobalt and manganese are both about 98% by the twenty-third hour. A feed extract solution can be completely depleted of substantially all cobalt and manganese without encountering a penalty of increased solution resistance because the metal depleted extract solution still contains large quantities of conductive ions of organic acid.

EXAMPLE 2

In this example of catalyst metal separation from TMA process residue, the same four channel stack used for Example 1 is used. The same stack operating conditions of 25 volts DC and 18 $mA/cm^2$ are used. However, residue feed solution is more concentrated in catalyst metals. The anolyte is 1000 ml of dilute sulfuric acid at 0.5 weight percent $H_2SO_4$ solution. The diluting solution is 550 ml of extract solution. The initial concentrating solution is 300 ml of hydrobromic acid at 1 weight percent HBr solution. The catholyte is 1000 ml of aqueous solution containing 4 weight percent acetic acid. The separation is conducted for 16 hours. Results of this separation are shown in TABLE III.

TABLE III

| METALS RECOVERY FROM TMA PROCESS RESIDUE | | | | | |
|---|---|---|---|---|---|
| | Feed Solution | | Metal Solution | | Recovery | Current |
| | Initial | Final | Initial | Final | % | Efficiency, % |
| Co | 0.400 | 0.077 | 0.000 | 0.400 | 87.3 | 10.9 |
| Mn | 0.262 | 0.044 | 0.000 | 0.268 | 89.3 | 7.9 |
| Ce | 0.163 | 0.071 | 0.000 | 0.118 | 63.1 | 1.4 |
| Na | 0.12 | — | 0.000 | 0.17 | 123.6 | 5.9 |
| Fe | 41 | 24 | 0 | 27 | — | — |
| Zr | <12 | <12 | 0 | <12 | — | — |

In TABLE III the concentrations for iron and zirconium are in parts per million by weight and all other concentrations are weight percent.

Catalyst metal and sodium recovery accounted for 26 percent of total current consumption. Recovered catalyst solution is very low in organic compound contamination. In this example contaminant concentrations in weight parts per million of solution are: 28 ppm benzoic acid, <5 ppm dimethylbenzoic acids, 46 ppm phthalic acids, 8 ppm methylphthalic acid, 5 ppm menimellitic acid and 300 ppm trimellitic acid.

The aqueous extract solution prepared for use in Example 2 is higher in cobalt and manganese content than the extract solution used in Example 1. Since the metal ions compete with hydrogen ions in the separation stack, higher current efficiencies with respect to catalyst metals generally can be obtained with a feed of higher catalyst metal content. The metal concentration in the product can be adjusted by varying the volume ratio or flow rate ratio of the feed extract solution to metal product solution. The maximum achievable concentration is limited by the electro-osmotic transport of water along with metal ions.

EXAMPLE 3

Example 2 was repeated with a current density of 36 mA/cm$^2$ instead of 18 mA/cm$^2$ there was a lower current efficiency. This decrease was due to more pronounced concentration polarization which occurred because of a greater mobility of co-ions in the membranes than in the solutions which resulted in: lower interfacial concentrations of ions on the entering side of the membrane and higher ion concentration on the other side of the membrane. Mass transfer limitation can be reached when current density becomes so high that interfacial ion concentration on the entering side approaches zero.

EXAMPLES 4 TO 8

Separations of these examples are conducted as in Example 2 except that 0.0, 0.003, 0.006, 0.008 and 0.20 weight parts of ethylene diaminetetra-acetic acid (EDTA) per weight part of TMA process residue are added when preparing the extract solutions. Current density is 22 mA/cm$^2$ instead of the 18 mA/cm$^2$ of Example 2. This effect of such use of EDTA is shown in TABLE IV.

TABLE IV

| EDTA: Residue Weight ratio | Metal Co, ppm | Product Mn, ppm | Solution FE ppm |
|---|---|---|---|
| 0:1 | 1314 | 626 | 62 |
| 0.003:1 | 1253 | 550 | <12 |
| 0.006:1 | 1233 | 556 | <12 |
| 0.008:1 | 1135 | 551 | <12 |
| 0.020:1 | 1024 | 579 | <12 |

By the use of only 0.003:1 weight ratio of EDTA to residue the transport of iron with cobalt and manganese can be substantially prevented.

In Table V to follow, equilibrium constants for EDTA complexes with various metals are given from "Chemistry of the Metal Chelate Compounds" by A. E. Martell; Prentice-Hall, (1952).

TABLE V

| EQUILIBRIUM CONSTANTS FOR EDTA AND METALS | |
|---|---|
| EDTA-METAL Complex | Equilibrium Constant, Keg. |
| $Co^{2+}$ | $10^{15}$ to $10^{16}$ |
| $Mn^{2+}$ | $10^{13}$ to $10^{14}$ |
| $Fe^{2+}$ | $10^{24}$ to $10^{25}$ |
| $Cu^{2+}$ | $10^{18}$ to $10^{19}$ |
| $Ni^{2+}$ | $10^{17}$ to $10^{18}$ |

Since the EDTA-metal equilibrium constants for iron, copper and nickel are all higher than the equilibrium constants for EDTA-cobalt and EDTA-manganese, EDTA added to the residue extract solution will prevent substantial transport of iron, copper and nickel with cobalt and manganese in the recovery of the latter two in a preferred embodiment of this invention.

EXAMPLES 9 TO 11

TABLE V

| COOLING AND SEPARATION TEMPERATURES FOLLOWING EXTRACTION | | | |
|---|---|---|---|
| Cooling and Separation Temperature, °C. | 26.7 | 32.2 | 37.8 |
| Solids Recovered, % of Residue | 31 | 29 | 27.1 |
| IPA product in Recovered Solids, Wt % | 90 | 94 | 94 |

EXAMPLE 12

A more complete component composition of one residue of IPA manufacture from a mixture of 85% m-xylene and 15% p-xylene and of the separated solid after cooling, the extract mixture to 26.7° C. is presented in Table VII.

TABLE VII

| COMPOSITION OF RESIDUE AND RECOVERED PRODUCT | | |
|---|---|---|
| Component, Wt % | Residue | Recovered Product |
| Benzoic Acid | 7.68 | 0.76 |
| m-and p-Toluic Acids | 5.30 | 0.13 |
| Dimethylbenzoic Acids | 0.06 | 0.00 |
| o-Phthalic Acid | 13.28 | 0.09 |
| IPA/TPA8 | 28.21 | 90.0 |
| 4-Methyl IPA | 0.17 | 0.02 |
| Benzyl Benzoate | 0.29 | 0.09 |
| Hemimellitic Acid | 3.26 | 0.03 |
| Trimellitic Acid | 11.51 | 0.73 |
| Dicarboxy Biphenyl | 1.62 | 0.07 |
| 1,2,3,5-Tetracarboxy Benzene | 0.86 | 0.04 |
| Tricarboxy Biphenyl | 9.76 | 3.92 |
| Tetracarboxy Biphenyl | 0.67 | 0.07 |
| 2,4',5-Tricarboxy Benzophenone | 0.27 | 0.02 |
| Others | 6.86 | 4.06 |

8 "IPA/TPA" is IPA product consisting of the lutectic mixture isophthalic acid and terephthalic acid.

From the data in Tables VI and VII, it is apparent that water extraction of the IPA process residue and cooling the resulting mixture to and separating it at a temperature of from 27° C. up to 50° C. causes 31 wt % to 27 wt % of the oxygen-containing aromatic compounds to be removed and 69 wt % to 72 wt % of those compounds to be dissolved. Those separated solids have an IPA product content representing at such 27° C. to 50° C. temperature range for cooling and separating the removal of 98 to 91% of IPA product from the residue. Such separated solids can be dissolved in some of the acetic acid wash liquor obtained from washing of IPA product recovered from the effluent from m-xylene oxidation. The resulting acetic acid solution can then be combined with such effluent to be cooled and decompressed to obtain IPA product and enhance its yield.

The rather broad spectrum of oxygen-containing aromatic compounds in the residue, illustrated in Table VII, result from the commercial oxidation of a xylene product containing 85% m-xylene isomer separated from a generally available mixture of the three isomeric xylenes. In some commercial oxidations, a rather pure m-xylene of 99 wt % m-xylene content, is oxidized. The other oxygen-containing aromatic compounds then becoming associated with IPA product and appearing in the IPA process residue are, of course, of a much narrower spectrum.

The water extraction of residue of TPA process does not dissolve as much of the para isomers of toluic acid, phthalic acid or carboxybenzaldehyde because they have solubilities of only 0.1 to 0.01 of the solubilities of the meta- or ortho-isomers. But, it is still desirable to effect separation of catalyst metal or metals from the dissolved oxygenated aromatic compounds. Here, too, the cooling and separation at cooler temperature of extract solution from insolubles is useful when starting with TPA process residue.

The extract solution, in addition to ions of metal oxidation catalyst (e.g., cobalt or cobalt and manganese), may also contain ions of one or more metals of corrosion present because the oxidation effluent, or acetic acid mother liquor, or a concentrate of the mother liquor or the hot fluid IPA process residue came into contact with apparatus (e.g., reaction or separation vessel or transfer conduits) which contained metal components which were fabricated from one or more types of stainless steel. Any of said fluids are sufficiently acidic to dissolve iron, nickel and/or chromium from apparatus. The electrodialysis comprising the main feature of the present invention can effect a useful selectivity of cobalt and/or manganese recovery vis-a-vis iron, nickel and/or chromium. Such selectivity of cobalt and/or manganese to iron, for example, is a separation ratio of 1.9:1. The separation ratio can be almost doubled by the use of a small amount of EDTA, for example, five weight parts per thousand weight parts of residue.

The following examples illustrate the main electrodialysis feature of the present invention.

EXAMPLE 13

In this example, the electrodialysis is conducted at 37.8° C. in a three compartment electrodialysis cell wherein the ion permeation membranes are of the aromatic type designated as the commercially available MC3470 and MC3475 membranes of Ionac. The compact widths are each 25 mm. The total effective area of the membranes is 55 cm$^2$, and the current density used is 21.5 mA/cm$^2$. Both electrodes are platinum. Such three compartment separation unit is operated in the batch recirculation mode using 1000 ml of initial feed solution containing 320 weight parts cobalt and 2620 weight parts of manganese per 10$^6$ weight parts of solution. There is used 300 ml of water for catalyst recovery solvent. The solution also contains TPA or IPA and associated co- and by-product oxygen-containing aromatic compounds. The results of eight hours of such batch recirculation operation are shown in Table VIII, to follow.

TABLE VIII

| CATALYST RECOVERY FROM AQUEOUS EXTRACT SOLUTION | | | | |
|---|---|---|---|---|
| Time, hrs | Volume, ml | Co, ppm | Mn, ppm | Fe, ppm |
| Extract Solution Feed | | | | |
| 0 | 1000 | 320 | 2620 | 54 |
| 2 | — | 197 | 1550 | — |
| 4 | — | 123 | 990 | — |
| 6 | — | 54 | 450 | — |
| 8 | 950 | 24 | 186 | 42 |
| Catalyst Metal Recovery Solution | | | | |
| 0 | 300 | 0 | 0 | — |
| 2 | — | 280 | 3050 | 0 |
| 4 | — | 580 | 4700 | — |
| 6 | 420 | 710 | 6100 | 46 |

After eight hours of operation, 93.2% of the cobalt and 97.8% of the manganese are recovered at a current efficiency of 3.4% for cobalt and 29.7% for manganese.

EXAMPLE 14

This example uses the same conditions and apparatus as used in Example 5, but uses 2860 ml of a more dilute feed solution with 300 ml of water as catalyst metal solvent, and conducts the batch recirculation mode for 22 hours. The results at 1 and 22 hours of operation are given in Table IX.

TABLE IX

| CATALYST METAL RECOVERY FROM AQUEOUS EXTRACT SOLUTION | | | | |
|---|---|---|---|---|
| Time, hrs | Volume, ml | Co, ppm | Mn, ppm | Fe, ppm |
| Extract Solution Feed | | | | |
| 0 | 2860 | 382 | 3200 | 42 |
| 22 | 2680 | 62 | 316 | 40 |
| Catalyst Metal Recovery Solution | | | | |
| 0 | 300 | 0 | 0 | 0 |
| 22 | 545 | 1700 | 16000 | 97 |

In this example, there are recovered 85% of the cobalt and 94% of the manganese at the respective current efficiencies of 3.9% and 38.6%.

EXAMPLE 15

In this example, the three compartment apparatus described in Example 5 is again used at 378° C., but is operated in the continuous mode at a current density of 21.5 mA/cm$^2$ with the feed solution flow at 11.6 cm/sec. After the feed solution had passed through the first time, it was fed again. This was repeated for a total of three passes. The results of this experiment is shown in Table X.

TABLE X

| CONTINUOUS CATALYST METAL RECOVERY | | | | |
|---|---|---|---|---|
| Pass | Cobalt | | Manganese | |
| No. | Conc, ppm | Recovery, % | Conc, ppm | Recovery, % |
| 0 | 242 | | 1980 | |
| 1 | 224 | 52.9 | 895 | 54.8 |
| 3 | 55 | 51.8 | 434 | 51.5 |
| Pass No. | Current Co, % | Efficiency Mn, % | | |
| 0 | 6.5 | 57.4 | | |
| 1 | 6.5 | 57.4 | | |
| 2 | 3.0 | 24.4 | | |
| 3 | 0.9 | 9.4 | | |

EXAMPLE 16

The process of Example 5 is repeated except that the batch recirculation electrodialysis is conducted at the temperature of 48.9° C. and ethylenediamine tetracitic acid (EDTA) is used to complex iron ions. The results of this example are shown in Table XI.

TABLE XI

| EDTA USE TO ENHANCE RATIO OF CATALYST METALS TO IRON | | | | | | | |
|---|---|---|---|---|---|---|---|
| | Extract Solution Fed | | | | Catalyst Metal Solution | | |
| Time hr | Vol., Ml | Co, ppm | Mn, ppm | Fe, ppm | Vol., Ml | Co, ppm | Mn, ppm | Fe, ppm |
| 0 | 500 | 174 | 1630 | 144 | 500 | 0 | 0 | 0 |
| 1 | 505 | — | — | | 510 | 92 | 840 | 24 |
| 2 | 510 | — | — | | 520 | 237 | 1290 | 46 |
| 3 | 510 | — | — | | 530 | 153 | 1420 | 37 |
| 4 | 520 | — | — | | 550 | 155 | 1480 | 31 |

TABLE XI-continued

EDTA USE TO ENHANCE RATIO OF
CATALYST METALS TO IRON

| | Extract Solution Fed | | | | Catalyst Metal Solution | | | |
|---|---|---|---|---|---|---|---|---|
| Time hr | Vol., Ml | Co, ppm | Mn, ppm | Fe, ppm | Vol., Ml | Co, ppm | Mn, ppm | Fe, ppm |
| 5 | 520 | <6 | 43 | 118 | 560 | 156 | 1470 | 36 |

The ratio of catalyst metal recovered to iron in Example 16 is 3.6:1.0.

EXAMPLE 17

This example includes extracting the residue with water, cooling and separating the resulting mixture, feeding the separated cool aqueous extract solution to electrodialysis, recovering therefrom the aqueous solution of catalyst metals and metal-free portion of the electrodialysis feed, using such metal-free portion of feed to extract additional residue, and repeating the steps of cooling and separating electrodialysis.

The electrodialysis cell used has a plurality of basic three compartment separation units wherein the cation and anion permeation membranes are, respectively, the MC3470 and the MC3475 products of Ionac.

Extraction

For the residue extraction 0.6 kg of fluid residue at 116° C. from IPA process containing 0.167 weight percent cobalt and 1.3 weight percent manganese (both calculated as free metals rather than their actual salt form) and 3.6 kg of water at the temperature of 27° C. are combined. The resulting mixture is at the temperature of 49° C.

Cooling and Solid-Liquid Separation

The resulting mixture of aqueous solution and insolubles at the temperature of 49° C. is cooled to the temperature of 27° C., and then filtered at the temperature of 27° C. The recovered solids amount to 0.445 kg on dry basis, and as dry solids contain 0.335 weight percent cobalt and 2.8 weight percent manganese. The filtrate amounts to 3.15 kg and contains 0.255 weight percent cobalt and 1.86 weight percent manganese. The 605 gram difference between feed to extraction and material removed from solid-liquid separation represent water in the separated solids and water flushed to steam by contact of residue with water.

Electrodialysis

The electrodialysis cell is operated in the batch recirculation mode. The 27° C. filtrate is fed as anolyte. The cell is operated at a current density of 21.5 mA/cm$^2$, and a temperature of 38° C. The catholyte contains 90 weight percent water and 10 weight percent acetic acid. The catalyst metal solvent feed to the central compartment is water used in the volume ratio to anolyte feed of 0.3:1.0. The aqueous solution exiting the central compartment contains 93% of the cobalt and 98% of the manganese in the anolyte feed. The aqueous solution exiting the anolyte compartment amounts to 31.5 kg and contains 0.018 weight percent cobalt and 0.037 weight percent manganese.

Second Extraction

The 3.15 kg of anolyte compartment effluent at 38° C. is combined with 0.45 kg of water at 10° C. and the resulting mixture (34.2° C.) is cooled to 27° C. The 27° C. aqueous mixture contains 0.0156 weight percent cobalt and 0.0325 weight percent manganese, and is contacted with 0.6 kg of 116° C. fluid IPA process residue.

Second Cooling and Separation

The resulting mixture at 49° C. is cooled to 27° C. and filtered. The filter cake amounts to 0.588 kg on dry basis which contains 0.35 weight percent cobalt and 2.82 weight percent manganese.

Second Electrodialysis

The second 27° C. filtrate is fed as anolyte to the same electrodialysis cell to which water is fed to the central compartment as solvent for recovered catalyst metal and aqueous (90% water) acetic acid is fed as the catholyte. The aqueous effluent from the central compartment contains 93% of the cobalt and 98% of the manganese in the anolyte feed.

The foregoing recycle of effluent from the anolyte compartment to extract additional IPA process residue can be repeated as many times as desired.

EXAMPLE 18

In this example, the electrodialysis cell consists of ten parallel repeating three compartment basic separation units wherein each of said units contains two cation permeable membranes (one to protect anode from bromide ions) and one anion permeable membrane. The anode is platinum plated on chromium, and the cathode is stainless steel. The compartment width is 0.1 cm. A tortuous flow path exists between inlet and outlet manifolds. The membranes are CZL and QZL membrane products of Ionics, Inc. The total effective membrane area is 2194 cm$^2$. The cell is operated at a current density of 21.5 mA/cm$^2$, and a temperature of 49° C.

The catholyte feed is aqueous (90 wt % water) acetic acid. The catalyst metal solvent is water fed to the compartments between the anolyte and catholyte compartments. The anolyte feed is aqueous acetic acid (90 wt.% water). The solution containing the catalyst metals contains bromide ions, as well as ions of cobalt, manganese and iron. The iron ions are from IPA process apparatus element corrosion. Cobalt, manganese and bromide ions are from the catalysis used in the air oxidation of liquid m-xylene dissolved in acetic acid. The bromide ions are converted to hydrogen bromide which is retained as dissolved bromide in the metal depleted feed in the liquid exiting the compartment between the two cation exchange membranes. The metals contents of such feed, and the effluent from the feed compartment, are shown in Table XII to follow.

TABLE XII

METAL IONS REMOVED FROM AQUEOUS SOLUTION
OF OXYGEN CONTAINING AROMATIC COMPOUNDS

| Time, Min. | Vol., ml | Co, ppm | Mn, ppm | Fe, ppm |
|---|---|---|---|---|
| Extract Solution Feed | | | | |
| 0 | 4700 | 263 | 2200 | 450 |
| 5 | 4700 | 210 | 1740 | 450 |
| 10 | 4700 | 164 | 1320 | — |
| 20 | 4650 | 92 | 763 | |
| 30 | 4650 | 38 | 330 | 378 |
| 40 | 4650 | 15 | 157 | 300 |
| Solution of Recovered Catalyst Metals | | | | |
| 0 | 1200 | 12 | 65 | 17 |
| 5 | 1280 | 182 | 1750 | — |
| 10 | 1350 | 355 | 3100 | 440 |
| 20 | 1470 | 530 | 4600 | |
| 30 | 1620 | 638 | 5500 | 570 |

TABLE XII-continued

METAL IONS REMOVED FROM AQUEOUS SOLUTION
OF OXYGEN CONTAINING AROMATIC COMPOUNDS

| Time, Min. | Vol., ml | Co, ppm | Mn, ppm | Fe, ppm |
|---|---|---|---|---|
| 40 | 1760 | 654 | 5400 | 600 |

The catalyst metals are recovered in the form of their acetates. The solution thereof, also contains acetic acid.

The aqueous solution of decreased catalyst metal concentration whose bromide ion contact has been converted into dissolved hydrogen bromide, can readily be treated to remove and recover the bromine. For example, such solution of decreased metal content at a temperature of 35° C. to 50° C. can be heated to a temperature of 80° C. to 100° C., stirred and injected with compressed air. The moist air evolving from the stirred solution contains hydrogen bromide which may be recovered as ammonium or sodium bromide or potassium bromide, or barium bromide by passing the hydrogen bromide and water-containing air into an apparatus solution of ammonium hydroxide, or sodium hydroxide, or potassium hydroxide, or barium hydroxide.

What is claimed is:

1. An electrodialysis process for recovery of cobalt and manganese ions from a diluting solution comprising said ions and contaminants, which comprises feeding said solution to an electrodialyzer separation stack which comprises an anode channel formed by an anode and a cation permeation membrane and at least one, three-channel repeating unit wherein each repeating unit having in sequence channels A, B, and C wherein this repeating unit comprises a Channel A formed by two cation permeation membranes, a Channel B formed by a cation permeation membrane and an anion permeation membrane, and a Channel C formed by an anion permeation membrane and either a cation permeation membrane or a cathode, passing an anolyte comprising an aqueous solution of an acid through the anode channel, feeding diluting solution through the A channels, feeding an electrolyte through the B channels, feeding a catholyte comprising an aqueous solution of a carboxylate produced by reaction of a metallic hydroxide and an organic acid selected from a group consisting of formic, acetic, oxalic, lactic, tartaric, citric, benzoic and phthalic acids in a concentration of at least about 0.01N, through the C channels and removing a concentrate comprising a solution of cobalt and manganese substantially free of contaminants as an effluent from the B channels.

2. The process of claim 1, wherein the anolyte is an aqueous solution of an acid selected from a group consisting of nitric acid, sulfuric acid, sulfurous acid, phosphoric acid, and boric acid at a concentration in the range of about 1N to about 0.01N and acetic acid and carbonic acid in a concentration of about 4 weight percent to about 20 weight percent.

3. The process of claim 1, wherein the electrolyte comprises a dilute aqueous solution of an acid selected from a group consisting of hydroiodic, hydrobromic, hydrochloric, nitric, sulfuric, sulfurous, phosphoric, hydrofluoric, acetic, carbonic, hydrocyanic and boric acids in a concentration of at least about 0.01N.

4. The process of claim 3, wherein the acid is hydrobromic acid at a concentration in the range of about 1N to about 0.01N.

5. The process of claim 1, wherein the acid is acetic acid at a concentration in the range of about 4 weight percent to about 20 weight percent.

6. The process of claim 1, wherein the anolyte comprises an aqueous solution of sulfuric acid, the electrolyte comprises an aqueous solution of hydrobromic acid, and the catholyte comprises an aqueous solution of acetic acid.

7. The process of claim 7, wherein each cation permeation membrane is polytetrafluorethylene modified by sulfonic acid groups bonded to carbon atoms of the polymer chain and each anion permeation membrane is an aminic sulfate modified polymer and the separation unit is operated at a current density of from about 5 mA/cm$^2$ to about 25 mA/cm$^2$.

8. The process of claim 1, wherein each cation permeation membrane is polytetrafluorethylene modified by sulfonic acid groups bonded to carbon atoms of the polymer chain and each anion permeation membrane is an aminic sulfate modified polymer.

9. The process of claim 1, wherein the separation unit is operated at a current density of from about 5 mA/cm$^2$ to about 25 mA/cm$^2$.

10. A process for recovery of cobalt and manganese ions from a diluting solution comprising said ions and contaminant ions of at least one metal selected from iron, copper, and nickel which recovery process comprises adding a complex forming compound to the diluting solution containing the metal ions; which comprises feeding said solution to an electrodialyzer separation stack which comprises an anode channel formed by an anode and a cation permeation membrane, and at least one, three-channel repeating unit wherein each repeating unit having in sequence channels A, B, and C wherein this separation stack comprises a Channel A formed by two cation permeation membranes, Channel B formed by a cation permeation membrane and an anion permeation membrane, and a Channel C formed by an anion permeation membrane and either a cation permeation membrane or a cathode, passing an anolyte comprising an aqueous solution of an acid through the anode channel, feeding diluting solution through the A channels, feeding an electrolyte through the B channels feeding a catholyte comprising an aqueous solution of a carboxylate produced by reaction of a metallic hydroxide and an organic acid selected from a group consisting of formic, acetic, oxalic, lactic, tartaric, citric, benzoic and phthalic acids in a concentration of at least about 0.01N, through the C channels and removing a concentrate comprising a solution of cobalt and manganese substantially free of contaminants as an effluent from the B channels wherein the complex-forming compound is added to the diluting solution prior to depletion of contaminant corrosion metals iron, or copper or nickel with cobalt and manganese ions from the diluting solution.

11. The process of claim 10, wherein the complex-forming compound is selected from the group consisting of ethylene diaminetetra-acetic acid, ammonia diacetic acid, and ammonia triacetic acid.

12. The process of claim 10, wherein the complex-forming compound is ethylene diamine tetra-acetic acid.

13. The process of claim 10, wherein the complex-forming compound is added to the diluting solution in the liquid state in an amount necessary to prevent substantially transport of contaminant corrosion metals iron, or copper or nickel with cobalt and manganese ions into the concentrating solution.

14. A method of separating cobalt ions or cobalt and manganese ions from an aqueous solution thereof also containing oxygen-containing aromatic compounds including benzoic acid, and one of the isomers of toluic acid, phthalic acid, and carboxybenzaldehyde which method comprises feeding such aqueous solution to an electrodialyzer separation stack which comprises an anode channel formed by an anode and a cation permeation membrane and at least one, three-channel repeating unit wherein each repeating unit having in sequence channels A, B, and C wherein this repeating unit comprises a Channel A formed by two cation permeation membranes, a Channel B formed by a cation permeation membrane and an anion permeation membrane, and a Channel C formed by an anion permeation membrane and either a cation permeation membrane or a cathode, passing an anolyte comprising an aqueous solution of about 4 percent to about 20 percent of acetic acid through the anode channel, feeding said aqueous solution through the A channels, feeding a dilute electrolyte comprising at least 0.1N HBr through the B channels, feeding an aqueous acetic acid solution at about 4 percent to about 20 percent concentration through the C channels and removing an aqueous effluent of decreased metal ion content from the A Channels, an aqueous solution of metal acetates as effluent from the B Channels and aqueous acetic acid of decreased acetic acid content as effluent from the C Channels.

15. The method of claim 14 conducted at a temperature of from 35° C. up to 50° C.

16. The method of claim 15 conducted with a current density of from 5 up to 45 milliamperes per square centimeter.

17. The method of claim 16 wherein the feed aqueous solution is at a temperature of from 25° C. up to 50° C.

18. The method of claim 15 conducted with a current density of from 15 up to 30 milliamperes per square centimeter.

19. The method of claim 18 wherein the feed aqueous solution is at a temperature of from 25° C. up to 50° C.

20. The method of claim 19 wherein ethylenediamine tetraacetic acid is added to the aqueous solution feed before it enters the electrodialysis.

21. The method of claim 19 wherein the aqueous feed solution is obtained by extracting a fluid isophthalic acid process residue having a temperature of from 100° C. to 110° C. or a concentrate thereof, fluid at a temperature of from 115° C. to 120° C. with water at a temperature of from 15° C. up to 35° C. at a water to residue weight ratio of from 1:1 up to 6:1 and separating from the resulting mixture the aqueous extract solution is said feed by means for solid-liquid separation.

22. The method of claim 20 wherein the mixture resulting from extraction is first cooled to a temperature of from 25° C. to 50° C. and at said temperature is subjected to means for solid-liquid separation.

* * * * *

UNITED STATES PATENT OFFICE
CERTIFICATE OF CORRECTION

Patent No. 4,680,098         Dated   July 14, 1987

Inventor(s)  Yuehsiung Chang

It is certified that error appears in the above-identified patent and that said Letters Patent are hereby corrected as shown below:

TITLE PAGE, IN THE ABSTRACT, column 2, line 25,
"Acetic acid and the catholyte" should be --acetic acid as the catholyte--

Column 5, Line 15, "th method" should be --the method--

Column 11, Line 62, "$Fe^{2+}$" should be --$Fe^{3+}$

Column 12, Line 6, "TABLE V" should be --TABLE VI--

Column 12, Line 25, "7.68" should be --17.68--

Column 14, Line 10, "1 and 22 hours" should be --0 and 22 hours--

Column 14, Line 60, "EDTA USE" should be --EDTA USED--

Column 15, Line 2, EDTA USE" should be --EDTA USED--

Column 17, Line 22, "apparatus solution" should read --aqueous solution--

Column 20, Line 25, "is said" should read --in said--

Signed and Sealed this

Tenth Day of November, 1987

*Attest:*

DONALD J. QUIGG

*Attesting Officer*              *Commissioner of Patents and Trademarks*